United States Patent [19]

Fisher et al.

[11] Patent Number: 5,015,630
[45] Date of Patent: May 14, 1991

[54] 5-OXIME AVERMECTIN DERIVATIVES

[75] Inventors: Michael H. Fisher, Ringoes; Helmut Mrozik, Matawan, both of N.J.

[73] Assignee: Merck & Co., Inc., Rahway, N.J.

[21] Appl. No.: 298,710

[22] Filed: Jan. 19, 1989

[51] Int. Cl.$^5$ .................. A61K 31/70; C07M 17/04
[52] U.S. Cl. .................................. 514/30; 514/450; 536/7.1; 549/264; 71/88
[58] Field of Search ............ 536/7.1; 514/30, 450; 549/264

[56] References Cited

U.S. PATENT DOCUMENTS

| | | |
|---|---|---|
| 4,199,569 | 4/1980 | Chabala et al. ............ 536/7.1 X |
| 4,201,861 | 5/1980 | Mrozik et al. ............... 536/7.1 |
| 4,206,206 | 6/1980 | Mrozik et al. ............ 536/7.1 X |
| 4,310,519 | 1/1982 | Albers-Schonberg et al. ...... 514/30 |
| 4,427,663 | 1/1984 | Mrozik ........................ 514/30 |
| 4,547,520 | 10/1985 | Ide et al. .................... 514/450 |
| 4,806,527 | 2/1989 | Christensen et al. ....... 536/7.1 X |
| 4,873,224 | 10/1989 | Linn et al. .................... 514/30 |
| 4,895,837 | 1/1990 | Mrozik et al. ................ 514/30 |

FOREIGN PATENT DOCUMENTS

| | | |
|---|---|---|
| 110667 | 6/1984 | European Pat. Off. .......... 549/264 |
| 214731 | 3/1987 | European Pat. Off. . |
| 238258 | 9/1987 | European Pat. Off. ........... 536/7.1 |
| 276131 | 7/1988 | European Pat. Off. . |
| 279783 | 8/1988 | European Pat. Off. .......... 549/264 |
| 285561 | 10/1988 | European Pat. Off. .......... 549/264 |
| 288205 | 10/1988 | European Pat. Off. .......... 549/264 |
| 142991 | 7/1985 | Japan ............................ 514/30 |

OTHER PUBLICATIONS

Schulman et al., "Demethylavermectins Biosynthesis, Isolation and Characterization", J. Antibiotics, 38, pp. 1494–1498 (1985).
Schulman et al., "'Streptomyces Avermitilis' Mutants Defective in Methylation of Avermectins", Antimicrob Agents Chemotherapy, 31, pp. 744–747 (1987).

*Primary Examiner*—Johnnie R. Brown
*Assistant Examiner*—Elli Peselev
*Attorney, Agent, or Firm*—David L. Rose; Joseph F. DiPrima

[57] ABSTRACT

Novel avermectin derivatives are disclosed, wherein the 5-hydroxy group is replaced by an oxime group. The avermectin-5-oximes can further be derivatized at the 4''- or 4'-positions as amino, substituted amino, acylhydrazone, semicarbazone, or substituted semicarbazone analogues. The avermectin-5-oximes are prepared by the oxidation of the 5-hydroxy compounds with manganese dioxide or with pyridinium dichromate to the known 5-oxo analogues, and these are then reacted with a hydroxylamine salt. The new compounds are potent anti-parasitic agents, in particular, the compounds are anthelmintic, insecticidal and acaricidal agents.

13 Claims, No Drawings

5-OXIME AVERMECTIN DERIVATIVES

BACKGROUND OF THE INVENTION

The term avermectin (previously referred to as C-076) is used to describe a series of compounds isolated from the fermentation broth of an avermectin producing strain of *Streptomyces avermitilis* and derivatives thereof. The morphological characteristics of the culture are completely described in U.S. Pat. No. 4,310,519. The avermectin compounds are a series of macrolides, each of which is substituted at the 13 position with a 4-(α-L-oleandrosyl)-α-L-oleandrose group. The avermectin compounds and the instant derivatives thereof have a very high degree of anthelmintic and anti-parasitic activity.

The avermectin series of compounds isolated from the fermentation broth have the following structure:

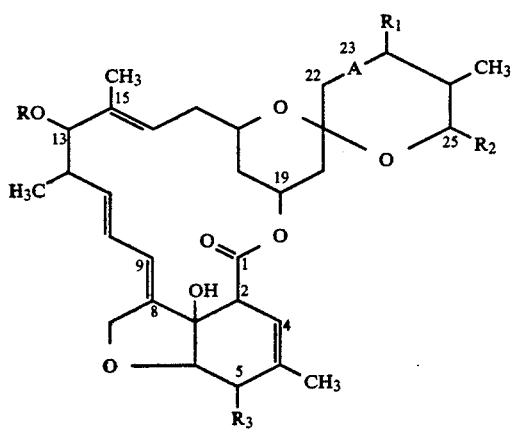

wherein $R_4$ is the 4'-(α-L-oleandrosyl)-α-L-oleandrosyl group of the structure:

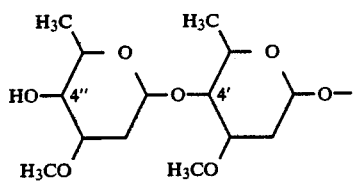

and wherein

A at the 22,23 position indicates a single or a double bond;

$R_1$ is a hydrogen or hydroxy and is present only when A indicates a single bond;

$R_2$ is iso-propyl or sec-butyl; and $R_3$ is methoxy or hydroxy

There are eight different avermectin natural product compounds and they are given the designations A1a, A1b, A2a, A2b, B1a, B1b, B2a, and B2b based upon the structure of the individual compounds.

In the foregoing structural formula, the individual avermectin compounds are as set forth below. (The R group is 4'-(α-L-oleandrosyl)-α-L-oleandrose):

|     | $R_1$(A)            | $R_2$      | $R_3$   |
| --- | ------------------- | ---------- | ------- |
| A1a | (22,23-double bond) | sec-butyl  | —OCH₃   |
| A1b | (22,23-double bond) | iso-propyl | —OCH₃   |
| A2a | —OH                 | sec-butyl  | —OCH₃   |
| A2b | —OH                 | iso-propyl | —OCH₃   |

-continued

|     | $R_1$(A)            | $R_2$      | $R_3$ |
| --- | ------------------- | ---------- | ----- |
| B1a | (22,23-double bond) | sec-butyl  | —OH   |
| B1b | (22,23-double bond) | iso-propyl | —OH   |
| B2a | —OH                 | sec-butyl  | —OH   |
| B2b | —OH                 | iso-propyl | —OH   |

The avermectin compounds are generaly isolated as mixtures of a and b components. Such compounds differ only in the nature of the $R_2$ substituent and the minor structural differences have been found to have very little effect on the isolation procedures, chemical reactivity and biological activity of such compounds.

In addition to these natural avermectins containing the 25-iso-propyl or 25-sec-butyl-substituent, closely related derivatives containing other branched or cyclic 25-alkyl or 25-alkenyl substituents, optionally further substituted by heteroatoms such as oxygen, sulfur, nitrogen, and halogen, are known in the literature. These derivatives are obtained through various adjustments and additions to the fermentation procedures as described fully in the European Patent Application EPO 0,214,731.

Avermectins are products of microbial fermentations using the actinomycete *Streptomyces avermitilis*. These microbes use acetates and propionates as building blocks for most of the avermectin carbon chain, which is then further modified by microbial enzymes to give the completed avermectin molecules. It is known, however, that the carbon C-25 and the 2-propyl and 2-butyl substituents at this carbon are not derived from acetate or propionate units, but are derived from aminoacids L-valine and L-isoleucine, respectively. It was reasoned, that these aminoacids are deaminated to the corresponding 2-keto acids, and that these then are decarboxylated to give 2-methylbutyric and 2-methylpentanoic acids. These acids then have been found to be directly incorporated into the avermectin structures to give the 2-propyl and 2-butyl C25 substituents, as is reported by Chen et al., *Abstr. Pap. Am. Chem. Soc.* (186 Meet.,MBTD 28, (1983)). It was also disclosed in European Patent Application number 0,214,731 that additions of large amounts of other acids such as cyclopentanoic, cyclobutyric, 2-methylpentanoic, 2-methylhexanoic, thiophene-3-carboxylic acids and others to the fermentation broth of *S. avermitilis* causes the microbes to accept these acids as substitutes and to make small amounts of avermectins containing these acids in form of new C-25 substituents. Examples of such avermectin derivatives are:

25-(thien-3-yl)-25-de-(1-methylpropyl)avermectin A2a
25-(cyclohex-3-enyl)-25-de-(1-methylpropyl)avermectin A2a
25-cyclohexyl-25-de-(1-methylpropyl)avermectin A2a
25-(1-methylthioethyl)-25-de-(1-methylpropyl)avermectin A2a
25-(2-methylcyclopropyl)-25-de-(1-methylpropyl)avermectin A2a Still additional avermectin derivatives are produced through artifical modification of the fermentation of *Streptomyces avermitilis* either by addition of metabolic inhibitors such as cinefungin (as described by Schulman et al., *J. Antibiot.* (1985), 38, 1494–1498) or by mutation of the parent strain (as described by Schulman et al., *Antimicrobial Agents and Chemotherapy*, (1987), 31, 744–747, and by EP 276-131-A to Pfizer INC.). Some of these avermectin derivatives are still further modified and are missing one or two of the 3'- and 3"-O-methyl groups (Schulman et al., *J. Antibiot.* (1985) 38, 1494–1498). Examples for such derivatives are:

3',3"-Bisdesmethylavermectin B1a/B1b.

3',3"-Bisdesmethylavermectin B2a/B2b.

3',3"-Bisdesmethyl-25-cyclohexyl-25-de-(2-butyl)-avermectin B2a

3',3"-Bisdesmethyl-25-cyclopentyl-25-de-(2-butyl)-avermectin B2a

3',3"-Bisdesmethyl-25-(3-thienyl)-25-de-(2-butyl)-avermectin B2a

3',3"-Bisdesmethyl-25-(3-furyl)-25-de-(2-butyl)-avermectin B2a

3',3"-Bisdesmethyl-25-(1-methylthioethyl)-25-de-(2-butyl)-avermectin B1a.

3"-desmethylavermectin B1a/B1b.

The fermentation products have been chemically modified in order to obtain further antiparasitic and insecticidal analogs with improved properties. Publications of such procedures in the scientific and patent literature have been reviewed by Fisher, M. H.; Mrozik, H. In *Macrolide Antibiotics*; Omura, S., Ed.; Academic: New York, (1984); pp 553–606, and by Davies, H. G.; Green, R. H. *Nat. Prod. Rep.*, (1986) 3, 87–121.

For example a group of semisynthetic avermectin derivatives were obtained by hydrogenating specifically the 22,23-double bond of avermectin B1 giving 22,23-dihydroavermectin B1 derivatives which have very potent anthelmintic and antiparasitic properties. Other examples of semisynthetic avermectin derivatives contain a 8,9-oxide group, a 4a-hydroxy or acyloxy group, a 23-keto group, which all are potent antiparasitic and insecticidal compounds.

It has also been described by Mrozik in U.S. Pat. No. 4,427,663 that amino substituents at the 4"- and 4'- positions have very high antiparasitic and insecticidal activities.

These compounds may be used as starting materials for the compounds of the instant invention without further modification, or when containing additional reactive groups, which are not to be modified under the reaction conditions applied, only after protection of such with a suitable protecting group.

SUMMARY OF THE INVENTION

The instant invention is concerned with derivatives of avermectin compounds wherein the 5-hydroxy group is replaced by an oxime substituent. The oxime analogs may also be further modified. Thus it is the object of this invention to describe such compounds. It is a further object of this invention to describe the processes useful for the preparation of such compounds. A still further object is to describe the use of such compounds as anthelmintic, insecticidal, and acaricidal agents. Still further objects will become apparent from the reading of the following description.

DESCRIPTION OF THE INVENTION

The compounds of the instant invention have the following structural formula:

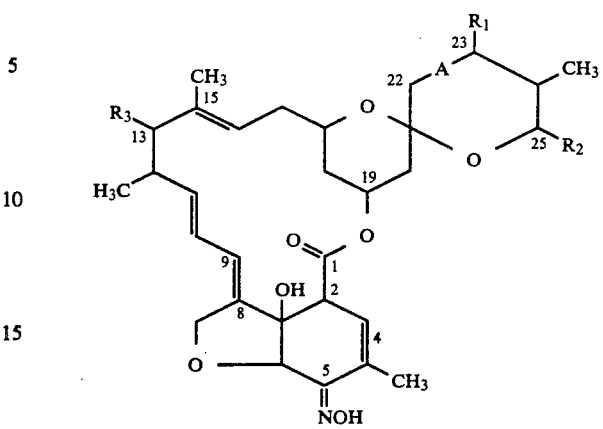

wherein

A at the 22,23 position represents a single bond and wherein $R_1$ is hydrogen or hydroxy or ketone, or A represents a double bond and $R_1$ is absent;

$R_2$ is an alpha-branched $C_3$–$C_8$ alkyl or alkenyl group, a $C_3$–$C_8$ cycloalkyl group, a $C_3$–$C_8$ cycloalkyl $C_1$–$C_3$ alkyl group, or a thienyl group.

$R_3$ is hydroxy, loweralkyloxy, loweralkanoyloxy, or

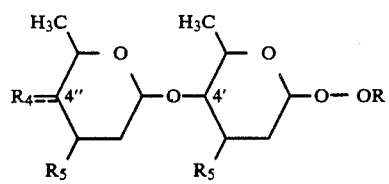

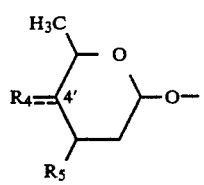

wherein $R_4$ is attached to C-4"or C-4' by a single bond and is hydroxy, amino, N-loweralkylamino, N,N-diloweralkylamino, loweralkanoylamino, N-loweralkylalkanoylamino or triloweralkylsilyloxy; or $R_4$ is attached to C-4" or C-4' by a double bond and is ketone, semicarbazone, N-loweralkylsemicarbazone, N,N-diloweralkylsemicarbazone, loweralkanoyl hydrazone, benzoylhydrazone, or loweralkylbenzoylhydrazone; and each R5 is independently hydroxy or methoxy.

Preferred compounds of the instant invention have the following structural formula:

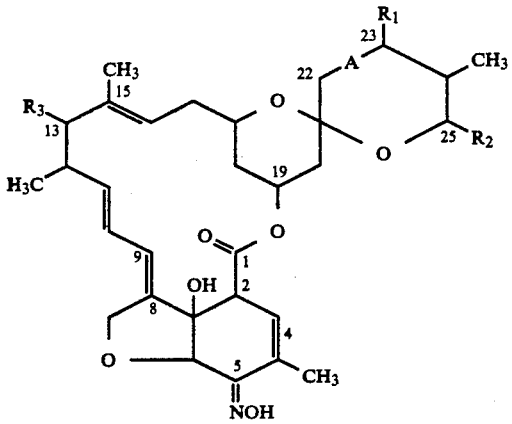

wherein

A at the 22,23 position represents a single bond and wherein $R_1$ is hydrogen or hydroxy or ketone, or A represents a double bond and $R_1$ is absent;

$R_2$ is an alpha branched $C_3$–$C_8$ alkyl or alkenyl group; and $R_3$ is hydroxy, loweralkyloxy, loweralkanoyloxy,

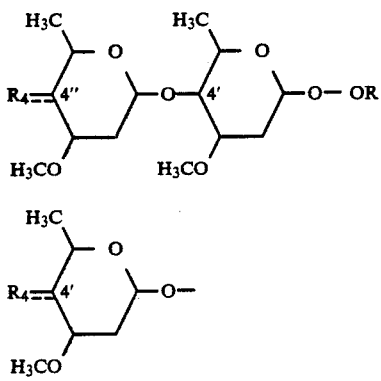

wherein $R_4$ is attached to C-4'' or C-4' by a single bond and is hydroxy, amino, N-loweralkylamino, N,N-diloweralkylamino, loweralkanoylamino, N-loweralkylalkanoylamino or triloweralkylsilyloxy; or $R_4$ is attached to C-4'' or C-4' by a double bond and is ketone, semicarbazone, N-loweralkylsemicarbazone, N,N-diloweralkylsemicarbazone, loweralkanoyl hydrazone, benzoylhydrazone, or loweralkylbenzoyl hydrazone.

Additional preferred compounds of the instant invention are realized in the foregoing structural formula wherein A at the 22,23 position represents a single bond and wherein $R_1$ is hydrogen or hydroxy, or A represents a double bond and $R_1$ is absent;

$R_2$ iso-propyl, sec-butyl, or an alpha-branched $C_3$–$C_8$ alkenyl group; and $R_3$ is

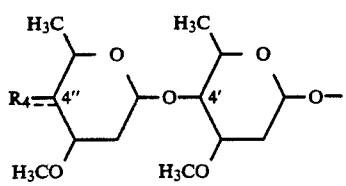

wherein $R_4$ is attached to C-4'' by a single bond and is hydroxy, amino, N-loweralkylamino, loweralkanoylamino, or N-loweralkylalkanoylamino;

The most preferred compounds are realized in the foregoing structural formula wherein A at the 22,23 position represents a single bond and wherein $R_1$ is hydrogen or hydroxy, or A represents a double bond and $R_1$ is absent;

$R_2$ iso-propyl, sec-butyl, or an alpha-branched $C_3$–$C_8$ alkenyl group; and $R_3$ is 4'-($\alpha$-L-oleandrosyl)-$\alpha$-L-oleandrosyloxy.

Preferred compounds of the instant invention are further realized in the following compounds:
4''-oxoavermectin B1a/B1b 5-ketoxime
avermectin B1a/B1b 5-ketoxime
4''-deoxy-4''-methylamino-avermectin B1a/B1b 5-ketoxime
4''-deoxy-4''-epi-methylamino-avermectin B1a/B1b 5-ketoxime
4''-amino-4''-deoxyavermectin B1a/B1b 5-ketoxime
4''-deoxy-4''-epi-amino-avermectin B1a/B1b 5-ketoxime
4''-acetylamino-4''-deoxyavermectin B1a/B1b 5-ketoxime
4''-deoxy-4''-epi-acetylamino-avermectin B1a/B1b 5-ketoxime
avermectin B1a/B1b 4''-semicarbazone 5-ketoxime
22,23-dihydro-avermectin B1a/B1b 5-ketoxime
22,23-dihydro-4''-oxo-avermectin B1/B1b 5-ketoxime
avermectin B2a/B2b 5-ketoxime
22,23-dihydro-4''-epi-acetylaminoavermectin B1a/B1b 5-ketoxime
22,23-dihydro-4''-deoxy-4''-methylamino avermectin B1a/B1b 5-ketoxime
4'-deoxy-4'-epi-methylamino-avermectin B1a/B1b monosaccharide 5-ketoxime
4''-epi-amino-4''-deoxyavermectin B2a/B2b 5-ketoxime
25-cylopentyl-25-de-(1-methylpropyl)-4''-oxo-avermectin B2a 5-ketoxime
25-cylopentyl-25-de-(1-methylpropyl)-avermectin B1a 5-ketoxime
25-cylopentyl-25-de-(1-methylpropyl)-4''-epi-avermectin B1a 5-ketoxime In the instant invention the term "loweralkyl" is intended to indicate those alkyl groups of from 1 to 6 carbon atoms such as methyl, ethyl, propyl, isopropyl, butyl, pentyl, hexyl, and the like.

The term "loweralkoxy" is intended to include those alkoxy groups of from 1 to 6 carbon atoms such as methoxy, ethoxy, propoxy, isopropoxy, butoxy, pentoxy, hexoxy, and the like.

The term "loweralkanoyl" is intended to include those alkanoyl groups of from 1 to 6 carbon atoms such as formyl, acetyl, propionyl, butyryl, pentanoyl, hexanoyl, and the like.

The term "halogen" is intended to include the halogen atoms, fluorine, chlorine, bromine, or iodine.

The above structural formula is shown without a definitive stereochemistry. However, during the course of the synthetic procedures used to prepare such compounds, the products of such procedures can be a mixture of stereoisomers. In particular, the stereoisomers at the 4''-, 4'-, 13-and 23-positions may be oriented either $\alpha$- or $\beta$- representing such groups being below or above the general plane of the molecule, respectively. In each such case both the $\alpha$- and $\beta$- configurations are intended to be included within the ambit of this invention. In certain cases the term "epi" is used to distinguish the stereoisomer being of opposite configuration to the natural compound at one specific assymmetrical carbon atom.

PREPARATION OF STARTING MATERIALS

The ultimate starting materials for the compounds of this invention are the avermectin fermentation products defined above. In addition, other microbially produced avermectin derivatives containing an alpha branched alkyl or alkenyl group substituent at the 25 position designated in the structural formula as $R_2$ have been described in European patent application number 86,305,604.0 (publication number 0,214,731), 88,300,426.9 (0,276,131), and 88300354.3 (0,276,103). These compounds can also be used as starting materials for the compounds claimed in this invention. The $R_2$ substituent is inert under the reaction conditions employed for the preparation of the compounds of this invention, so that these reactions can also be carried out with these altered avermectin derivatives. It is apparent that additional reactions are required to prepare the starting materials for the instant compounds. Specifically reactions are carried out at the 4", 4', 22, and 23-positions. It is generally preferred to prepare whatever substituents are required at these positions before the oxidation at the 5-hydroxy group, and subsequent substitution on the thus produced 5-ketone. Such a procedure generally avoids undesirable side reactions. This technique is not required however, and if desired other sequences may be used. In addition, during the oxidation and substitution reactions described above, it is necessary to protect the hydroxy group at the 5-position to avoid oxidation or substitution at such position. With this position protected the reactions may be carried out at the 4"- or 4'-positions without affecting the remainder of the molecule. Subsequent to any of the above described reactions the protecting group may be removed and the unprotected product isolated. The protecting group employed is ideally one which may be readily synthesized, will not be affected by the reactions at the 4"- and 4'-positions and may be removed without affecting any other functionality of the molecule. One preferred type of protecting group for the avermectin type of molecule is the tri-substitiuted silyl group, preferably the triloweralkyl silyl group. In addition such compounds have significant activity and are considered to be within the scope of this invention. One especially preferred example is the t-butyldimethylsilyl group. The reaction preparing the protected compound is carried out by reacting the hydroxy compound with the appropriately substituted silylhalide, preferably the silylchloride in an aprotic polar solvent such as methylene chloride, benzene, toluene, ethyl acetate, tetrahydrofuran, dimethylformamide and the like. In order to minimize side reactions, there is included in the reaction mixture a base to react with the acid halide released during the course of the reaction. Preferred bases are amines such as imidazole, pyridine, or triethylamine. The base is required in amounts equimolar to the amount of hydrogen halide liberated; however, generally several equivalents of the amine are employed. The reaction is stirred at from 0° C. to the reflux temperature of the reaction mixture and is complete in from ½ to 16 hours.

The silyl group is removed by stirring the silylated compound in methanol catalized by an acid preferably a sulfonic acid monohydrate such as p-toluenesulfonic acid monohydrate. The reaction is complete in about 1 to 12 hours at from 0° to 50° C. Alternatively, the silyl group may be removed by treatment of the silyl compound with anhydrous pyridine-hydrogen fluoride in tetrahydrofuran. The reaction is complete in from 3 to 24 hours at from 0° to 25° C.

Another of the starting materials used in the foregoing reaction scheme are those in which the 22,23-double bond has been reduced to a single bond. The preferred catalyst for the selective hydrogenation of the 22,23-double bond is one having the formula:

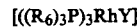

wherein
$R_6$ is loweralkyl, phenyl, or loweralkyl substituted phenyl and Y is halogen. The reduction is completely described in U.S. Pat. No. 4,199,569.

The other starting materials which are used in the above reaction scheme involve the preparation of the monosaccharide. The processes which may be used to prepare the monosaccharide derivatives of the avermectin compounds are described in U.S. Pat. No. 4,206,205. The reaction consists generally of treating the starting disaccharide with acid in an aqueous organic solvent mixture. Water concentration of from 0.1 to 20% by volume and acid concentrations of from about 0.01 to 0.1% will predominantly produce the monosaccharide.

A further procedure for the preparation of the monosaccharide utilizes a 1% mineral acid solution in isopropanol at 20° to 40° C. for from 6 to 24 hours. Mineral acids such as sulfuric, phosphoric, and the like may be employed.

In all cases the substituent at the 25-position of the avermecin is inert to the reaction conditions and the presence of alkyl groups, alkenyl groups, cycloalkyl groups, cycloalkenyl groups and the like at this position will little affect the preparation, isolation, or activity of the avermectin derivative.

In the isolation of the avermectin compounds, which serve as starting materials for the instant process, from the fermentation broth, the various avermectin compounds will be found to have been prepared in unequal amounts. In particular an "a" series compound will be prepared in a higher proportion than the corresponding "b" series and "b" series is constant throughout the avermectin compounds and consists of a sec-butyl group and an iso-propyl group respectively at the 25 position. This difference, of course, does not interfere with any of the instant reactions. In particular it may not be necessary to separate the "b" components from the related "a" component. Separation of these closely related compounds is generally not practiced since the "b" compound is present only in a very small percent by weight, and the structural difference has negligible effect on the reaction processes and biological activities.

In particular it has been found that the starting materials for the compounds of this invention are very often prepared in a ratio of about 80% of the avermectin "a" or major component and 20% of the avermectin "b" or minor compounds. Thus the preferred composition of this invention is one which contains more than about 80% of the "a" component and less than about 20% of the "b" component.

PREPARATION OF COMPOUNDS

The preparation of the instant compounds requires that the avermectin starting materials be oxidized at the 5-position to the corresponding ketones, which are then treated with a salt of hydroxylamine, preferably a hydrochloride. The 4''-, 4'-, and 23-hydroxy groups are less reactive and the 7-hydroxy group is very unreactive and they need not be protected. The oxidation reaction is carried out in an inert solvent such as ether, methylene chloride, or dimethylformamide using manganese dioxide ($MnO_2$) or pyridinium dichromate as the oxidizing agent. Since these are rather mild reagents and reaction conditions, and the 5-hydroxy group is very reactive, these two synthetic steps can be conducted in the presence of other substituents attached to the molecule. Thus hydroxy-, amino-, alkylamino-, acylamino-, acylhydrazone-, semicarbazone- substituents at the 4''- , 4'-, or 23-positions of the avermectin molecule generally need not be protected during this conversion. The 5-keto and 5-oxime compounds are isolated using techniques known to those skilled in the art. It generally is not neccessary to isolate the 5-keto compound and the crude oxidation product may be reacted immediately with an hydroxylamine salt in order to afford the desired oxime derivatives. The reaction with the hydroxylamine salt is generally carried out in a solvent, preferably a polar solvent, such as an alkanol like ethanol, and is generally completed in from one half to six hours.

The starting materials containing oxo-, amino-, alkylamino-, or acylamino-substituents at the 4''- or 4'-positions are described by Mrozik in U.S. Pat. No. 4,427,663, and those containing 4''- or 4'-O-acyl-substituents by Mrozik et al. in U.S. Pat. No. 4,201,861. 4''- and 4'-semicarbazone and acylhydrazone derivatives are obtained from the known 4''- and 4'-oxo derivatives by reaction with semicarbazides or hydrazones according to well known procedures. Thus the preparation of 4''-oxoavermectin-4''-semicarbazones is carried out by treatment of 4''-oxoavermectin B1a/B1b with a semicarbazide in a polar solvent such as methanol, ethanol, tetrahydrofuran, and the like in the presence of a catalytic amount of acid, preferably acetic acid, at temperatures ranging fron $-20°$ to $30°$ C. for a period of 0.5 to 20 hour. The corresponding semicarbazones are isolated and purified by techniques known to those skilled in the art.

Alternatively avermectin 5-oxime compounds can be further modified.

All of the foregoing reactions carried out at the 4''-position of the avermectin can be carried out at the 4'-position of the monosaccharide to afford the correspondingly substituted monosaccharide derivatives.

The novel compounds of this invention have significant parasiticidal activity as anthelmintics, ectoparasiticides, insecticides, and acaracides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats, and poultry. Among the helminths the group of worms described as nematodes causes widespread and oftentimes serious infection in varios species of animals. The most common genera of nematodes infecting the animals referred to above are Haemonchus, Trichostrogylus, Ostertagia, Nematodirus, Cooperia, Ascaris, Bunostomum, Oesophagostomum, Chabertia, Trichuris, Strongylus, Trichonema, Dictocaulus, Capillaria, Heterakis, Toxocara, Ascaridia, Oxyuris, Ancylostoma, Uncinaria, Toxascaris, and Parascaris. Certain of these, such as Nematodirus, Cooperia, and Oesophagostomum attack primarily the intestinal tract while others, such as Haemonchus and Ostertagia, are more prevalent in the stomach while still others such as Dictocaulus are found in the lungs. Still other parasites may be located in other tisues and organs of the body such as the heart and blood vessels, subcutaneous and lymphatic tissue and the like. The parasitic infections known as helminthiasis lead to anemia, malnutrition, weakness, weight loss, severe damage to the walls of the intestinal tract and other tissues and organs and, if left untreated, may result in the death of the infected host. The avermectin compounds of this invention have unexpectedly high activity against Dirofilaria in dogs, Nematospiroides, Syphacia, Aspiculuris in rodents, anthropod ectoparasties of animals and birds such as ticks, mites, lice, fleas, blowfly, in sheep Lucilia sp., biting insects and such migrating dipterous larvea as Hypoderma sp. in cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extraintestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica*.

The compounds are also useful against insect pests of stored grains such as Tribolium sp., Tenebrio sp. and of agricultural plants such as spider mites (Tetranychus sp.) aphids (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contain from about 0.001 to 5% by weight of the active compound. Preferred drench formulations may contain from 0.01 to 0.1% by weight active compound. The capsules or boluses are comprised of the active ingredient admixed with a carrier vehicle such as starch, talc, magnesium stearate, or di-calcium phosphate.

Where it is desired to administer the avermectin derivatives in a dry, solid unit dosage form, capsules, boluses, or tablets containing the desired amount of active compound usually are employed. The dosage forms are prepared by intimately and uniformly mixing the active ingredients with suitable finely divided diluents, fillers, disintegrating agents, and/or binders such as starch, lactose, talc, magnesium stearate, vegetable gums and the like. Such unit dosage formulations may be varied widely with respect to their total weight and content of antiparasitic agent depending upon factors such as the type of host animal to be treated, the severity and type of the infection and the weight of the host.

When the active compound is to be admnistered via the animal feedstuff, it is intimately dispersed in the feed or used as a top dressing or in the form of pellets which may then be added to the finished feed or optionally fed separately. Alternatively, the antiparasitic compounds of our invention may be administered to the animals parenterally, for example, by intraruminal, intramuscular, intratracheal, or subcutaneous injection in which the active ingredient is dissolved or dispersed in a liquid carrier vehicle. For parenteral administration, the active material is suitably admixed with an acceptable vehicle, preferably of the vegetable oil variety such as peanut oil, cotton seed oil, and the like. Other parenteral vehicles such as organic preparations using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis,they are also useful in the prevention and treatment of diseases caused by other parasites, for example, arthropod parasites such as ticks, lice, fleas, mites, and other biting insects in domesticated animals and poultry. They are also effective in treatment of parasitic diseases that occur in other animals including humans. The optimum amount to be employed for the best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administratering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field. When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for the direct feeding to the animal or for addition to the feed either directly or after an intermediate dilution or blending step. Typical carriers or diluents suitable for such compositions include, for example, distillers dried grains, corn meal, citrus meal, fermentaion residues, ground oyster shells, wheat shorts, molasses solubles, corn cob meal, edible bean mill feed, soya grits, crushed limestone and the like. The active avermectin compounds are intimately dispersed throughout the carrier by methods such as grinding, stirring, milling, or tumbling. Compositions containing from about 0.005 to 2.0% weight of the active compound are particularly suitable as feed premixes. Feed supplements, which are fed directly to the animal, contain from about 0.002 to 0.3% by weight of the active compounds.

Such supplements are added to the animal feed in an amount to give the finished feed the concentration of active compound desired for the treatment and control of parasitic diseases. Although the desired concentration of the active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

In using the compounds of this invention, the individual avermectin components may be prepared and used in that form. Alternatively, mixtures of two or more of the indivdual avermectin components may be used, or other active compounds not related to the compounds of this invention.

The compounds of this invention are also useful in combatting agricultural pests that inflict damage upon crops while they are growing or in storage. The compounds are applied using known techniques as sprays, dusts, emulsions and the like, to the growing or stored crops to effect protection from such agricultural pests.

The following examples are provided in order that this invention might be more fully understood; they are not to be construed as limitative of the invention.

The avermectin derivatives prepared in the folowing examples are generally isolated as amorphous solids and not as crystalline solids. They are thus characterized analytically using techniques such as mass spectrometry, nuclear magnetic resonance spectrometry and the like. Being amorphous, the compounds are not characterized by sharp melting points, however, the chromatographic and analytical methods employed indicate that the compounds are pure.

EXAMPLE 1

4''-Deoxy-4''-epi-methylamino-5-oxoavermectin B1a/B1b

A solution of 500 mg of 4''-deoxy-4''-epi-methylaminoavermectin B1a/B1b (obtained as described in preparations A, B, C, and D) in 50 ml of ether was stirred with 3.0 g of activated manganese dioxide at room temperature for 18 hours. Then the product was isolated by dilution of the reaction mixture with ethyl acetate and filtration through a sintered glass funnel. The $MnO_2$ was washed repeatedly with methylene chloride. The filtrate was combined and concentrated in vacuo to 381 mg of light colored glass, which was shown to be 95 % pure by high performance liquid chromatography and was characterized by its mass and $^1$H-NMR spectra as 4''-deoxy-4''-epi-methylamino-5-oxoavermectin B1a/B1b.

EXAMPLE 2

4''-Deoxy-4''-epi-methylaminoavermectin B1a/B1b 5-ketoxime.

A solution of 380 mg of 4''-deoxy-4''-epi-methylamino-5-oxoavermectin B1a/B1b, 1.5 ml of dry pyridine, and 300 mg of hydroxylamine hydrochloride in 15 ml of dry ethanol was stirred 2.5 hours at room temperature. Then the ethanol was removed in vacuo at room temperature, and the residue was distributed between water and ethyl acetate. The ethyl acetate extract was washed with water, dried with MgSO$_4$, and concentrated in vacuo to 395 mg of yellow glass. Purification by silica gel column chromatography with methylene chloride containing from 2.5 to 7.5 % of methanol gave a 140 mg fraction containing the desired product. Further purification by preparative silica gel layer chromatography using a methylene chloride methanol (9:1) solvent mixture afforded 105 mg of pure 4''-deoxy-4''-epi-methylaminoavermectin B1a/B1b 5-ketoxime as a foam, which was characterized by its mass and $^1$H-NMR spectra.

EXAMPLE 3

Avermectin B1a/B1b 5-ketoxime.

A solution containing 131 mg of 5-oxo-avermectin B1a/B1b (described in *J Agric. Food Chem.* (1981), 29, 884–886) in 5.0 ml of absolute ethanol, 0.5 ml of pyridine, and 104 mg of hydroxylamine hydrochloride was stirred at room temperature for 3.5 hours. The reaction mixture was concentrated in vacuo at room temperature to a thick oil. This was dissolved in ether, and the solution was washed with water, dried over MgSO$_4$, and concentrated in vacuo to 140 mg of light foam. Purification by preparative silica gel layer chromatography with a methylene chloride-methanol (ratio 92.5:7.5) solvent mixture gave 72.5 mg of avermectin B1a/B1b 5-ketoxime, which was characterized by its mass and $^1$H-NMR spectra.

EXAMPLE 4

Avermectin B2a/B2b 5-ketoxime.

5-Oxo-avermectin B2a/B2b (described in *J. Agric. Food Chem.* (1981), 29, 884–886) is reacted according to the procedure fully described in Example 3 to give avermectin B2a/B2b 5-ketoxime, which is characterized by its mass and $^1$H-NMR spectra.

EXAMPLE 5

22,23-Dihydroavermectin B1a/B1b 5-ketoxime.

A solution containing 130 mg of 22,23-dihydro-5-oxoavermectin B1a/B1b (described in Anal. Chem. (1987), 59, 266–270) is reacted with 105 mg of hydroxylamine hydrochloride and 0.5 ml of pyridine in 5 ml of dry ethanol as fully described in Example 3 to give 22,23-dihydroavermectin B1a/B1b 5-ketoxime, which is characterized by its mass and NMR spectra.

EXAMPLE 6

4''-Epi-acetylamino-4''-deoxy-5-oxoavermectin B1a/B1b.

A solution of 100 mg of 4''-epi-acetylamino-4''-deoxyavermectin B1a/B1b (from preparation G) in 3.5 ml of anhydrous dimethylformamide was stirred with 82 mg of pyridinium dichromate at room temperature for 45 minutes. The reaction was worked up with water and ether, and the washed ether phase was concentrated in vacuo to 98 mg of colorless glass, which was characterized by its mass and NMR spectra as 4''-epi-acetylamino-4''-deoxy-5-oxoavermectin B1a/B1b.

EXAMPLE 7

4''-Epi-acetylamino-4''-deoxyavermectin B1a/B1b ketoxime.

A solution of 98 mg of crude 4''-epi-acetylamino-4''-deoxy-5-oxoavermectin B1a/B1b, 75 mg of hydroxylamine hydrochloride, and 0.36 ml of pyridine in 3.6 ml of ethanol was stirred at room temperature for 75 minutes. Then the reaction mixture was concentrated in vacuo to a solid residue. This was worked up with water and ethyl acetate, and the organic phase was dried and concentrated in vacuo to 96 mg of solid residue. Purification by preparative reverse phase high performance liquid chromatography on a Waters Magnum 20 column and 75% acetonitrile-methanol-3:2 mixture and 25 % water gave 46 mg of 4''-epi-acetylamino-4''-deoxyavermectin B1a/B1b 5-ketoxime, which was characterized by its mass and NMR spectra.

EXAMPLE 8

22,23-Dihydro-5-oxoavermectin B1a/B1b 4''-semicarbazone.

A solution of 500 mg of 22,23-dihydro-4''-oxoavermectin B1a/B1b semicarbazone (obtained as described in preparations H, I, and J) in 50 ml of ether is stirred with 3.0 g of activated manganese dioxide at room temperature for 18 hours. Then the product is isolated by dilution of the reaction mixture with ethyl acetate and filtration through a sintered glass funnel. The MnO$_2$ is washed repeatedly with methylene chloride. The filtrate is combined and concentrated in vacuo to a light colored glass, which is characterized by its mass and $^1$H-NMR spectra as 22,23-dihydro-5-oxoavermectin B1a/B1b 4''-semicarbazone.

EXAMPLE 9

22,23-Dihydroavermectin B1a/B1b 4''-semicarbazone-5-ketoxime.

A solution containing 130 mg of 22,23-dihydro-5-oxoavermectin B1a/B1b 4''-semicarbazone (obtained in Example 8) in 5.0 ml of absolute ethanol, 0.5 ml of pyridine, and 105 mg of hydroxylamine hydrochloride is stirred at room temperature for 3.5 hours. The reaction mixture is concentrated in vacuo at room temperature to a thick oil. This is dissolved in ether, and the solution is washed with water, dried over MgSO$_4$, and concentrated in vacuo to a light foam. Purification by preparative silica gel layer chromatography gives 22,23-dihydroavermectin B1a/B1b 4''-semicarbazone-5-ketoxime, which is characterized by its mass and $^1$H-NMR spectra.

EXAMPLE 10

5-Oxoavermectin B1a/B1b 4''-acetylhydrazone.

A solution of 500 mg of avermectin B1a/1b 4''-acetylhydrazone (obtained as described in preparations K and L) in 50 ml of ether is stirred with 3.0 g of activated manganese dioxide at room temperature for 18 hours. The product is isolated by dilution of the reaction mixture with ethyl acetate and filtration through a sintered glass funnel. The MnO$_2$ is washed repeatedly with methylene chloride. The filtrate is combined and concentrated in vacuo to a light colored glass, which is characterized by its mass and $^1$H-NMR spectra as 5-oxoavermectin B1a/B1b 4''-acetylhydrazone.

EXAMPLE 11

Avermectin B1a/B1b 4''-acetylhydrazone-5-ketoxime.

A solution containing 130 mg of 5-oxoavermectin B1a/B1b 4"-acetylhydrazone (obtained in Example 10) in 5.0 ml of absolute ethanol, 0.5 ml of pyridine, and 105 mg of hydroxylamine hydrochloride is stirred at room temperature for 3.5 hours. The reaction mixture is concentrated in vacuo at room temperature to a thick oil. The residue is dissolved in ether, and the solution is washed with water, dried over MgSO$_4$, and concentrated in vacuo to a light foam. Purification by preparative silica gel layer chromatography gives avermectin B1a/B1b 4"-acetylhydrazone-5-ketoxime, which is characterized by its mass and $^1$H-NMR spectra.

PREPARATION A

5-O-t-Butyldimethylsilylavermectin B1a/B1b.

A solution of 50 g of avermectin B1a/B1b (dried over P$_2$O$_5$ in high vacuum to constant weight), 24 g of imidazole and 24 g of tert-butyldimethylsilyl chloride in 400 ml of anhydrous dimethylformamide was stirred at room temperature for 50 minutes. The reaction mixture was poured into 1.5 l of ice cold water and the aqueous phase was extracted four times with 200 ml of ether. The organic phase was washed twice with water, aqueous sodium chloride solution, dried with magnesium sulfate and concentrated in vacuo to a white foam. The crude product was purified by silica gel column chromatography with a methylene chloride-ethyl acetate 90:10 to 70:30 solvent system to give 46.5 g of 5-O-t-butyldimethylsilylavermectin B1a/B1b as an amorphous foam, which was characterized by its $^1$H-NMR- and mass spectra.

PREPARATION B

5-O-t-Butyldimethylsilyl-4"-oxoavermectin B1a/B1b.

To a solution containing 9.1 ml of oxalyl chloride in 230 ml of dry methylene chloride stirred at −60° C. was added 15 ml of dry dimethylsulfoxide dissolved in 120 ml of dry methylene chloride during 15 min. Then a solution of 46.5 g of 5-O-t-butyl-dimethylsilylavermectin B1a/B1b dissolved in 230 ml of dry methylene chloride was added over a period of 15 minutes while maintaining the temperature at −60° C. The reaction mixture was stirred at this temperature for 30 minutes when 65 ml of dry triethylamine was added. The mixture was stirred for 5 additional minutes at −60° C, and then the cooling bath was removed and the reaction mixture was allowed to come to ambient temperature. After addition of water the reaction product was extraxted with methylene chloride, the extract was washed with water, dried and concentrated in vacuo to 45.5 g of a yellow foam. This was identified by its mass and NMR spectra as 5-O-t-butyldimethylsilyl-4"-oxoavermectin B1a/B1b, which was used for further chemical reactions without purification.

PREPARATION C

5-O-t-Butyldimethylsilyl-4"-deoxy-4"-epi-methylamino-avermectin B1a/B1b

A solution of 26 ml of glacial acetic acid in 300 ml of MeOH was treated with methylamine gas at 0° C. until the pH of the solution reached 9.0. To this a solution containing 44.5 g of 5-O-t-butyldimethylsilyl-4"-oxoavermectin B1a/B1b in 200 ml of methanol was added, and the reaction mixture was stirred at room temperature for 1 hour, when a solution of 3.5 g of sodium-cyanoborohydride in 75 ml of MeOH was added dropwise over 10 min. After 50 min the reaction mixture was poured into 1.5 l of cold aqueous Na$_2$CO$_3$ solution and the product was extracted with ether. The extract was washed with water, dried, and concentrated in vacuo to 44.8 g of yellow foam. Thin layer chromatography (silica gel, methylene chloride-ethyl acetate 85:15) of the crude product at this point showed several spots. Further purification by silica gel column chromatography using methylene chloride-ethyl acetate solvent mixtures gave 4.7 g of 4"-epi-5-O-t-butyldimethylsilylavermectin B1a/B1b, 1.2 g of 5-O-t-butyldimethylsilyl-4"-deoxy-4"-methylaminoavermectin B1a/B1b, and 14 g of 5-O-t-butyldimethylsilyl-4"-deoxy-4"-epi-methylaminoavermectin B1a/B1b as light foams, which were characterized by their mass spectrum and their $^1$H-, and $^{13}$C-NMR specta.

PREPARATION D

4"-Deoxy-4"-epi-methylaminoavermectin B1a/B1b.

A solution of 14 g of 5-O-t-butyldimethylsilyl-4"-deoxy-4"-epi-methylaminoavermectin B1a/B1b in 200 ml of methanol and a solution of 7 g of p-toluenesulfonic acid monohydrate in 500 ml of methanol was mixed and stirred at room temperature for 45 minutes, and then poured into dilute aqueous Na$_2$CO$_3$ solution. The product was extracted with ethyl acetate, washed with water and dried over MgSO$_4$, concentrated in vacuo, and purified by preparative silica gel column chromatography with a methylene chloride-methanol 95:5 solvent mixture to give 6.7 g of 4"-deoxy-4"-epi-methylaminoavermectin B1a/B1b, which was identified by NMR and mass spectra.

PREPARATION E

4"-epi-Amino-5-O-t-butyldimethylsilyl-4"-deoxy-avermectin B1a/B1b.

For the reductive amination 12 mg of sodium cyanoborohydride was added to a solution of 200 mg of 5-O-t-butyldimethylsilyl-4"-oxoavermectin B1a/B1b (from preparation B) and 160 mg of ammonium acetate in 3 ml of methanol, and the reaction mixture was stirred at room temperature for 1 hour. Then it was poured into aqueous Na$_2$CO$_3$ solution, and the organic products were extracted with ethyl acetate. The extract was washed with water, dried, and concentrated in vacuo to 210 mg of yellow oil. Preparative silica gel layer chromatography with 98:2 methylene chloride-methanol solvent gave 26 mg of 4"-amino-5-O-t-butyldimethylsilyl-4"-deoxyavermectin B1a/B1b, and 100 mg of 4"-epi-amino-5-O-t-butyl-dimethylsilyl-4"-deoxyavermectin B1a/B1b as light foams, which were characterized by their mass and their $^1$H-, and $^{13}$C-NMR spectra.

PREPARATION F

4"-epi-Amino-4"-deoxyavermectin B1a/B1b.

A solution of 100 mg of 4"-epi-amino-5-O-t-butyl-dimethylsilyl-4"-deoxyavermectin B1a/B1b (from preparation E) in 10 ml of methanol containing 1% of p-toluenesulfonic acid monohydrate was kept at room temperature for 30 minutes and then poured into aqueous NaHCO$_3$ solution. The product was isolated by extraction with ethyl acetate, and obtained in pure form after preparative silica gel layer chromatography as 55 mg of a light yellow foam, which was characterized by its mass and NMR spectra as 4"-epi-amino-4"-deoxyavermectin B1a/B1b.

PREPARATION G

4"-epi-Acetylamino-4"-deoxyavermectin B1a/B1b.

A solution of 50 mg of 4"-epi-amino-4"-deoxyavermectin B1a/B1b in 0.5 ml of methylene chloride was treated with 0.007 ml of acetic anhydride at room temperature for 1 hour. The reaction mixture was then diluted with ethyl acetate and washed with dilute NaHCO₃ solution and water, and was dried and concentrated in vacuo to a white foam, which was characterized by its mass spectrum and $^1$H-NMR spectrum as 4"-epi-acetylamino-4"-deoxyavermectin B1a/B1b.

PREPARATION H 22,23-Dihydro-4"-oxo-5-O-tert-butyldimethylsilylavermectin B1a/B1b.

To a solution of 97 μl of oxalyl chloride in 2.5 ml of methylene chloride stirred at −60° C. a solution of 160 μl of dimethylsulfoxide in 1.0 ml of methylene chloride was added dropwise over 3 minutes from a syringe. Then a solution of 500 mg of 22,23-dihydro-5-O-tert-butyldimethylsilyl-avermectin B1a/B1b in 3.0 ml of methylene chloride was added by syringe dropwise during 5 minutes. The reaction mixture was stirred at −60° C. for 30 minutes, when 0.71 ml of triethylamine was added dropwise. After another 5 minutes at −60° C. the cooling bath was removed, and the reaction mixture was allowed to come to room temperature. Addition to water, extraction with ether, washing with water, drying and concentration in vacuo gave 520 mg of a yellow foam, which was purified by preparative silica gel layer chromotagraphy with a methylene chloride-ethyl acetate-9:1 solvent mixture to give 470 mg of pure 22,23-dihydro-4"-oxo-5-O-tert-butyldimethylsilyl-avermectin B1a/B1b, which was characterized by its mass and 300 mHz $^1$H-NMR spectra.

PREPARATION I 22,23-Dihydro-4"-oxo-5-O-tert-butyldimethylsilyl-avermectin B1a/B1b semicarbazone.

A solution of 3.0 ml of MeOH containing 22,23-dihydro-4"-oxo-5-O-tert-butyldimethylsilylavermectin B1a/B1b (50 mg), semicarbazide hydrochloride (14.3 mg), and sodium acetate (15 mg) was stirred at room temperature for 2 hours. Then addition of 4 ml of water, extraction with ether, washing with water, drying and concentration in vacuo gave 58 mg of crude product. Purification by preparative silica gel layer chromatography with a methylene chloride-methanol-95:5 solvent mixture gave 37 mg of pure 22,23-dihydro-4"-oxo-5-O-tert-butyldimethylsilyl-avermectin B1a/B1b semicarbazone, which was characterized by its mass and $^1$H-NMR spectra.

PREPARATION J 22,23-Dihydro-4"-oxo-avermectin B1a/B1b semicarbazone.

A solution of 35 mg of 22,23-dihydro-4"-oxo-5-O-tert-butyldimethylsilyl-avermectin B1a/B1b semicarbazone in 3.5 ml of MeOH containing 1 % of p-toluenesulfonic acid monohydrate was held at room temperature for 60 minutes. Addition of aqueous NaHCO3 solution, extraction with ether, washing with water, drying and concentrating in vacuo gave 23 mg of crude product. Purification by preparative silica el layer chromatography using a methylene chloride-methanol-94:6 solvent mixture afforded 5.2 mg of pure 22,23-dihydro-4"-oxo-avermectin B1a/B1b semicarbazone, which was characterized by its mass and $^1$H-NMR spectra.

PREPARATION K

4"-Oxoavermectin B1a/1b.

A cold (0° to 5° C.) solution of 5.50 gm (5.40 mMole), 5-O-tert-butyl-dimethylsilyl-4"-oxoavermectin B1a/1b (obtained through preparation B), and methanolic 1.0% p-toluenesulfonic acid monohydrate, 120 mL (6.2 mMole), was stirred for 50 minutes and then poured into aqueous sodium bicarbonate. The product was extracted with methylene chloride. The methylene chloride solutions were combined, dried over anhydrous sodium sulfate and evaporated under reduced pressure providing 4.5 gm of 4"-oxoavermectin B1a/1b which was characterized by nuclear magnetic resonance, mass spectra [871 (M+H)+] and high pressure liquid chromatographic analyses.

PREPARATION L

4"-Oxoavermectin B1a/1b acethydrazone.

A solution of 4"-oxoavermectin B1a/1b, 200 mg, acethydrazide, 34 mg, glacial acetic acid, 24 μL, and pyridine, 100 μL in 1.2 μL of methanol was stirred at room temperature, 23° C, for 19 hours and then evaporated under reduced pressure. The residue was taken up in methylene chloride, extracted with aqueous sodium bicarbonate, dried over sodium sulfate and evaporated under reduced pressure. The residue was chromatographed on a column of silica gel using 1.0 to 3.0% methanol in methylene chloride furnishing 101 mg of 4"-oxoavermectin B1a/1b acethydrazone which was characterized by nuclear magnetic resonance, mass spectra and high pressure liquid chromatographic analyses.

What is claimed is:

1. A compound having the formula:

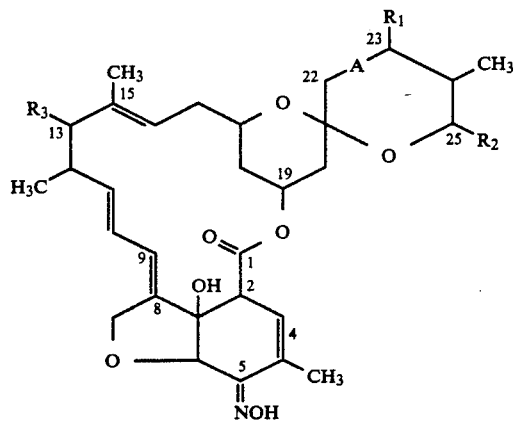

wherein A at the 22,23 position represents a single bond and wherein $R_1$ is hydrogen or hydroxy or keto, or A represents a double bond and $R_1$ is absent;

$R_2$ is an alpha-branched $C_3$-$C_8$ alkyl;

$R_3$ is

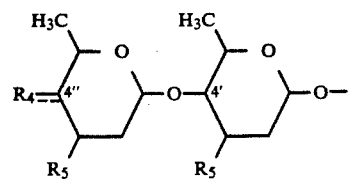

wherein $R_4$ is attached to C-4" by a single bond and is hydroxy, amino, N-methyl, N-ethyl, N-propyl, N-isopropyl or N-n-butyl amino; N,N-dimethyl, NN-diisopropyl or N,N-di-n-butyl amino; loweralkanoylamino, or N-loweralkylalkanoylamino; or R₄ is attached to C-4-41 or C-4' by a double bond and is semicarbazono, N-loweralkylsemicarbazono, N,N-diloweralkylsemicarbazano, loweralkanoylhydrazono, benzoylhydrazono, or loweralkylbenzoylhydrazono, and each R₅ is independently hydroxy or methoxy.

2. A compound of claim 1 having the formula:

[Chemical structure diagram showing avermectin-type compound with labels CH₃, R₃, H₃C, OH, O, NOH, CH₃, R₁, R₂, and numbered positions 1, 2, 4, 5, 8, 9, 13, 15, 19, 22, 23, 25, A]

wherein A at the 22,23 position represents a single bond and wherein R₁ is hydrogen or hydroxy or keto or A represents a double bond and R₁ is absent;

R₂ is an alpha-branched C₃-C₈ alkyl and

R₃ is

[Chemical structure showing disaccharide moiety with H₃C, H₃CO, O, R₄, 4", 4' labels]

wherein R₄ is attached to C-4" by a single bond and is hydroxy, amino, N-methyl, N-ethyl, N-propyl, N-isopropyl or N-n-butyl amino; N,N-dimethyl, N,N-diethyl, N,N-dipropyl, N,N-diisopropyl or N,N-di-n-butylamino; loweralkanoylamino, or N-loweralkylalkanoylamino; or R₄ is attached to C-4" or C-4' by a double bond and is semicarbazono, N-loweralkylsemicarbazono, N,N-diloweralkyl-semicarbazono, loweralkanoylhydrazono, benzoylhydrazono, or loweralkylbenzoylhydrazono.

3. A compound of claim 2, wherein A at the 22, 23 position represents a single bond and wherein R1 is hydrogen or hydroxy, or A represents a double bond and R1 is absent;

R2 is iso-propyl or sec-butyl; and

R3 is

[Chemical structure showing disaccharide moiety with H₃C, H₃CO, O, R₄, 4", 4' labels]

wherein R₄ is attached to C-4" or C-4' by a single bond and is hydroxy, amino, N-methyl, N-ethyl, N-propyl, N-isopropyl or N-n-butyl amino; loweralkanoylamino, or N-loweralkylalkanoylamino.

4. The compound of claim 1, which is 4"-deoxy-4"-epi-methylamino-avermectin B1a/B1b 5-ketoxime.

5. The compound of claim 1, which is 4"-deoxy-4"-epi-acetylamino-avermectin B1a/B1b 5-ketoxime.

6. The compound of claim 1, which is 4"-amino-4"-deoxyavermectin B1a/B1b 5-ketoxime.

7. The compound of claim 1, which is 22,23-dihydroavermectin B1a/B1b-4"-semicarbazone 5-ketoxime.

8. A compound of claim 3, wherein A at the 22, 23 position represents a single bond and wherein R₁ is hydrogen or hydroxy, or A represents a double bond and R₁ is absent;

R₂ is iso-propyl or sec-butyl and

R₃ is 4'(α-L-oleandrosyl)-α-L-oleandrosyloxy.

9. The compound of claim 1 which is avermectin B1a/B1b 5-ketoxime.

10. The compound of claim 1 which is 22,23-dihydroavermectin B1a/B1b 5-ketoxime.

11. A method for the treatment of parasitic infections of plants, which comprises treating the infected plant, or the soil in which the infected plant grows with an effective amount of a compound of claim 1.

12. A method for the treatment of parasitic infections of animals, which comprises treating the infected animal with an effective amount of a compound of claim 1.

13. A composition useful for the treatment of animals or plants infected with parasites, which comprises an inert carrier and an effective amount of a compound of claim 1.

* * * * *